United States Patent
Graham et al.

(10) Patent No.: US 7,418,749 B2
(45) Date of Patent: Sep. 2, 2008

(54) PATIENT CARE EQUIPMENT SUPPORT LOCK

(75) Inventors: Mark Alan Graham, Springboro, OH (US); Michael E. Cerimele, Indianapolis, IN (US); Christian H. Reinke, York, SC (US); David C. Newkirk, Lawrenceburg, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 318 days.

(21) Appl. No.: 10/575,405

(22) PCT Filed: Oct. 12, 2004

(86) PCT No.: PCT/US2004/033647

§ 371 (c)(1),
(2), (4) Date: Apr. 10, 2006

(87) PCT Pub. No.: WO2005/037165

PCT Pub. Date: Apr. 28, 2005

(65) Prior Publication Data

US 2007/0138354 A1 Jun. 21, 2007

Related U.S. Application Data

(60) Provisional application No. 60/510,756, filed on Oct. 13, 2003.

(51) Int. Cl.
*A61G 7/05* (2006.01)
*A47C 21/00* (2006.01)

(52) U.S. Cl. ................ 5/503.1; 5/600; 5/658; 248/158; 248/159

(58) Field of Classification Search ............ 5/600, 5/658, 503.1, 81.1 R; 248/158, 159, 125.1, 248/125.8
See application file for complete search history.

(56) References Cited

U.S. PATENT DOCUMENTS

| 4,725,027 A | 2/1988 | Bekanich ............ 248/125.8 |
| 4,945,592 A | 8/1990 | Sims et al. ............ 5/658 |
| 5,078,349 A | 1/1992 | Smith .............. 248/125.8 |
| 5,094,418 A | 3/1992 | McBarnes, Jr. et al. .. 248/286.1 |
| 5,135,191 A | 8/1992 | Schmuhl ............ 248/125.1 |
| 5,306,109 A | 4/1994 | Kreuzer et al. .......... 414/343 |
| 5,366,191 A | 11/1994 | Bekanich ............ 248/125.1 |
| 5,400,995 A | 3/1995 | Boyd ................ 248/414 |

(Continued)

FOREIGN PATENT DOCUMENTS

WO    WO 92/18085    10/1992

(Continued)

*Primary Examiner*—Robert G Santos
(74) *Attorney, Agent, or Firm*—Barnes & Thornburg LLP (57) ABSTRACT

An equipment support includes an equipment supporting portion to support patient care equipment, a downwardly extending coupler coupled to the equipment supporting portion, an upper lock and a lower lock. The coupler has upper and lower portions configured for receipt in upper and lower sockets, respectively. The upper lock moves to a locking position to lock the upper portion to the upper socket as the lower lock moves to an unlocking position to unlock the lower portion from the lower socket. The upper lock moves to an unlocking position to unlock the upper portion from the upper socket as the lower lock moves to a locking position to lock the lower portion to the lower socket.

26 Claims, 6 Drawing Sheets

U.S. PATENT DOCUMENTS

| | | | |
|---|---|---|---|
| 5,407,163 A | 4/1995 | Kramer et al. | 248/291.1 |
| 5,527,125 A | 6/1996 | Kreuzer et al. | 403/325 |
| 5,876,016 A | 3/1999 | Urban et al. | 248/159 |
| 6,036,147 A | 3/2000 | Miilitzer | 248/159 |
| 6,056,249 A | 5/2000 | Fillon, Jr. | 248/125.7 |
| 6,109,572 A | 8/2000 | Urban et al. | 248/159 |
| 6,375,133 B1 | 4/2002 | Morrow | 248/125.8 |
| 6,619,599 B2 | 9/2003 | Elliott et al. | 248/125.8 |
| 7,065,811 B2 * | 6/2006 | Newkirk et al. | 5/600 |
| 7,065,812 B2 * | 6/2006 | Newkirk et al. | 5/600 |
| 7,216,382 B2 * | 5/2007 | Newkirk et al. | 5/600 |
| 7,254,850 B2 * | 8/2007 | Newkirk et al. | 5/600 |
| 2004/0199996 A1 | 10/2004 | Newkirk et al. | 5/81.1 R |
| 2005/0000019 A1 | 1/2005 | Newkirk et al. | 5/600 |
| 2006/0031989 A1 * | 2/2006 | Graham et al. | 5/610 |
| 2006/0207025 A1 * | 9/2006 | Newkirk et al. | 5/600 |
| 2006/0207026 A1 * | 9/2006 | Newkirk et al. | 5/600 |
| 2006/0242763 A1 * | 11/2006 | Graham et al. | 5/503.1 |
| 2007/0069093 A1 * | 3/2007 | Graham et al. | 248/231.71 |
| 2007/0138354 A1 * | 6/2007 | Graham et al. | 248/121 |
| 2007/0187559 A1 * | 8/2007 | Newkirk et al. | 248/125.8 |
| 2007/0251014 A1 * | 11/2007 | Newkirk et al. | 5/658 |

FOREIGN PATENT DOCUMENTS

| | | |
|---|---|---|
| WO | WO 00/09061 | 2/2000 |
| WO | WO2005/037164 | 4/2005 |

* cited by examiner

PATIENT CARE EQUIPMENT SUPPORT LOCK

CROSS-REFERENCE TO RELATED APPLICATIONS

This application is a U.S. national application under 37 C.F.R. § 371(b) of International Application Serial No. PCT/US2004/033647 filed Oct. 12, 2004, which claims the benefit under 35 U.S.C. § 119(e) of U.S. Provisional Patent Application Ser. No. 60/510,756 filed Oct. 13, 2003.

FIELD OF THE INVENTION

The present disclosure relates to a system for supporting patient care equipment adjacent to a patient support such as a hospital bed, and more particularly relates to a system for supporting patient care equipment that facilitates transfer of patient care equipment between a patient support, such as a hospital bed, a stretcher, an ambulatory care chair, and the like, and a support structure, such as a service column, a wall-mounted equipment support arm, a stand, a cart, a headwall, a wall of a hospital room, and the like.

BACKGROUND OF THE INVENTION

Hospitalized patients often require patient care equipment to be in close proximity during hospital care. Such patient care equipment is typically supported on a patient care equipment support. Illustratively, patient care equipment includes any one or more of the following: heart monitoring equipment, medical gas delivery equipment, infusion management equipment, intra-venous bags, equipment monitors, patient monitors, defibrillators, IV poles, and the like, many of which directly connect to the patient via lines or tubes.

It is desirable that patient care equipment is transferable between a patient support, such as a hospital bed, a stretcher, an ambulatory care chair, and the like, and a support structure, such as a service column, a wall-mounted equipment support arm, a stand, a cart, a headwall, a wall of a hospital room, and the like.

SUMMARY OF THE INVENTION

The present invention comprises one or more of the following features or elements in the appended claims or combinations thereof.

An equipment support is transferable between a first device having an upper socket and a second device having a lower socket. Illustratively, the equipment support includes an equipment supporting portion configured to support patient care equipment, a downwardly extending coupler coupled to the equipment supporting portion, an upper lock and a lower lock.

Illustratively, the upper and lower locks are configured to prevent accidental release of the equipment support from the upper socket until the equipment support is seated properly in the lower socket and locked thereto. Likewise, the upper and lower locks are configured to prevent accidental release of the equipment support from the lower socket until the equipment support is seated properly in the upper socket and locked thereto.

The coupler illustratively has upper and lower portions configured for receipt in the upper and lower sockets, respectively. The upper lock moves to a locking position to lock the upper portion to the upper socket as the lower lock moves to an unlocking position to unlock the lower portion from the lower socket. The upper lock moves to an unlocking position to unlock the upper portion from the upper socket as the lower lock moves to a locking position to lock the lower portion to the lower socket.

Each of the upper and lower locks may have a locking element and a locking member that moves to wedge the locking element against a respective one of the upper and lower sockets when the upper and lower locks are in their respective locking positions. Illustratively, each lock comprises a plurality of balls and a locking cylinder having a tapered portion that drives the locking balls radially outwardly to engage a locking groove in a respective one of the upper and lower sockets when the lock is in its locking position.

The lower portion of the coupler may have an opening at a bottom end thereof. The upper lock may include a rod coupled to the upper locking member and extending downwardly therefrom. An end of the rod spaced from the upper locking member may be accessible through the opening so that an upper lock release button enters the opening and engages the rod as the lower portion seats downwardly into the lower socket to unlock the upper portion from the upper socket.

Illustratively, the upper lock release button is a protrusion in the lower socket. The coupler may include an outer tube having a bore. The upper locking member and the rod may be received in the bore of the tube.

Each of the coupler upper and lower portions may vary in diameter from a large diameter to a small diameter in a downward direction. The small diameter of the upper portion may be equal to or larger than the large diameter of the lower portion. Illustratively, each of the coupler upper and lower portions is frustoconical. The coupler may have a generally cylindrical intermediate portion separating the coupler upper and lower portions.

Each socket may be upwardly opening. Each socket opening may vary in diameter from a large diameter to a small diameter in a downward direction. The small diameter of the upper socket opening may be equal to or larger than the large diameter of the lower socket opening. Illustratively, each of the upper and lower socket openings is frustoconical.

The first device may be any one of the following: an arm, a column, a cart, a stand, a hospital bed, a surgery table and a stretcher. The second device may be any one of the following: an arm, a column, a cart, a stand, a hospital bed, a surgery table and a stretcher. The equipment support may carry any one or more of the following: heart monitoring equipment, medical gas delivery equipment, infusion management equipment, intra-venous bags, equipment monitors, patient monitors, defibrillators and IV poles.

Thus, a patient care equipment support is transferable between a first device having an upper tapered socket and a second device having a lower tapered socket. Illustratively, the equipment support includes an equipment supporting portion configured to support patient care equipment, a downwardly extending post coupled to the equipment supporting portion, an upper lock and a lower lock. The post has upper and lower tapered portions configured for receipt in upper and lower tapered sockets, respectively. The upper lock moves to a locking position to lock the upper tapered portion to the upper tapered socket as the lower lock moves to an unlocking position to unlock the lower tapered portion from the lower tapered socket. The upper lock moves to an unlocking position to unlock the upper tapered portion from the upper tapered socket as the lower lock moves to a locking position to lock the lower tapered portion to the lower tapered socket.

Features of the present disclosure will become apparent to those skilled in the art upon consideration of the following detailed description of illustrative embodiments exemplifying the best mode of carrying out the present disclosure as presently perceived.

BRIEF DESCRIPTION OF THE DRAWINGS

The detailed description particularly refers to the accompanying figures, in which.

DESCRIPTION OF THE ILLUSTRATIVE EMBODIMENTS

For the purposes of promoting an understanding of the principles of the present invention, reference will be made to a number of illustrative embodiments shown in the accompanying drawings and the following description thereof.

Figures 1, 2, 9:
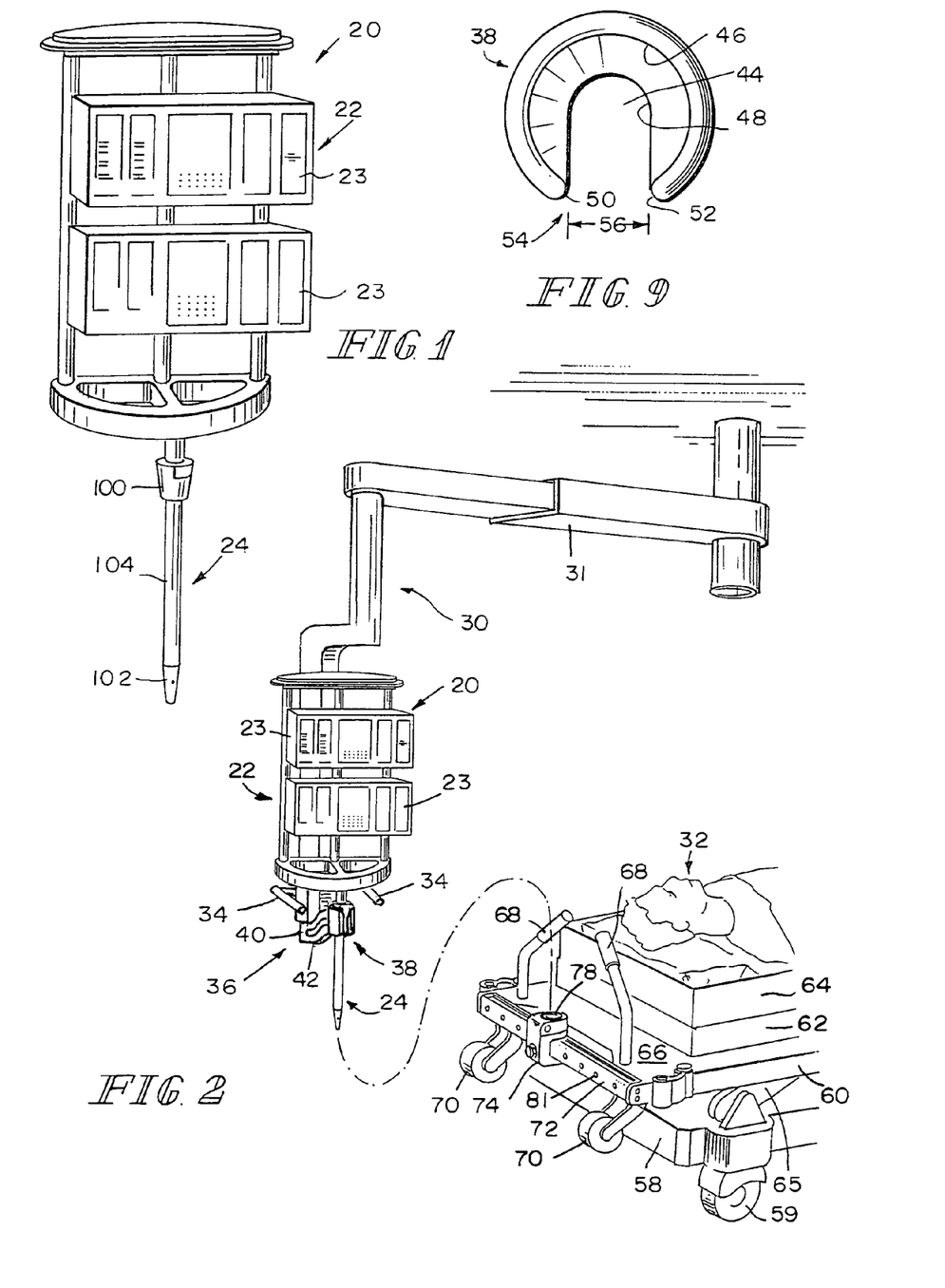
FIG. 1 is a partial perspective view of an equipment support including an equipment supporting portion configured to support patient care equipment and a downwardly extending post coupled to the equipment supporting portion, the post including a cylindrical intermediate portion disposed between upper and lower portions.
FIG. 2 is a perspective view showing the equipment support adapted to be transferable between a service column having an upper socket and a hospital bed having a lower socket.
FIG. 9 is plan view of upper socket having a generally c-shaped cross section having spaced apart end portions defining an outwardly opening slot in communication with a central bore.
Figure 3:
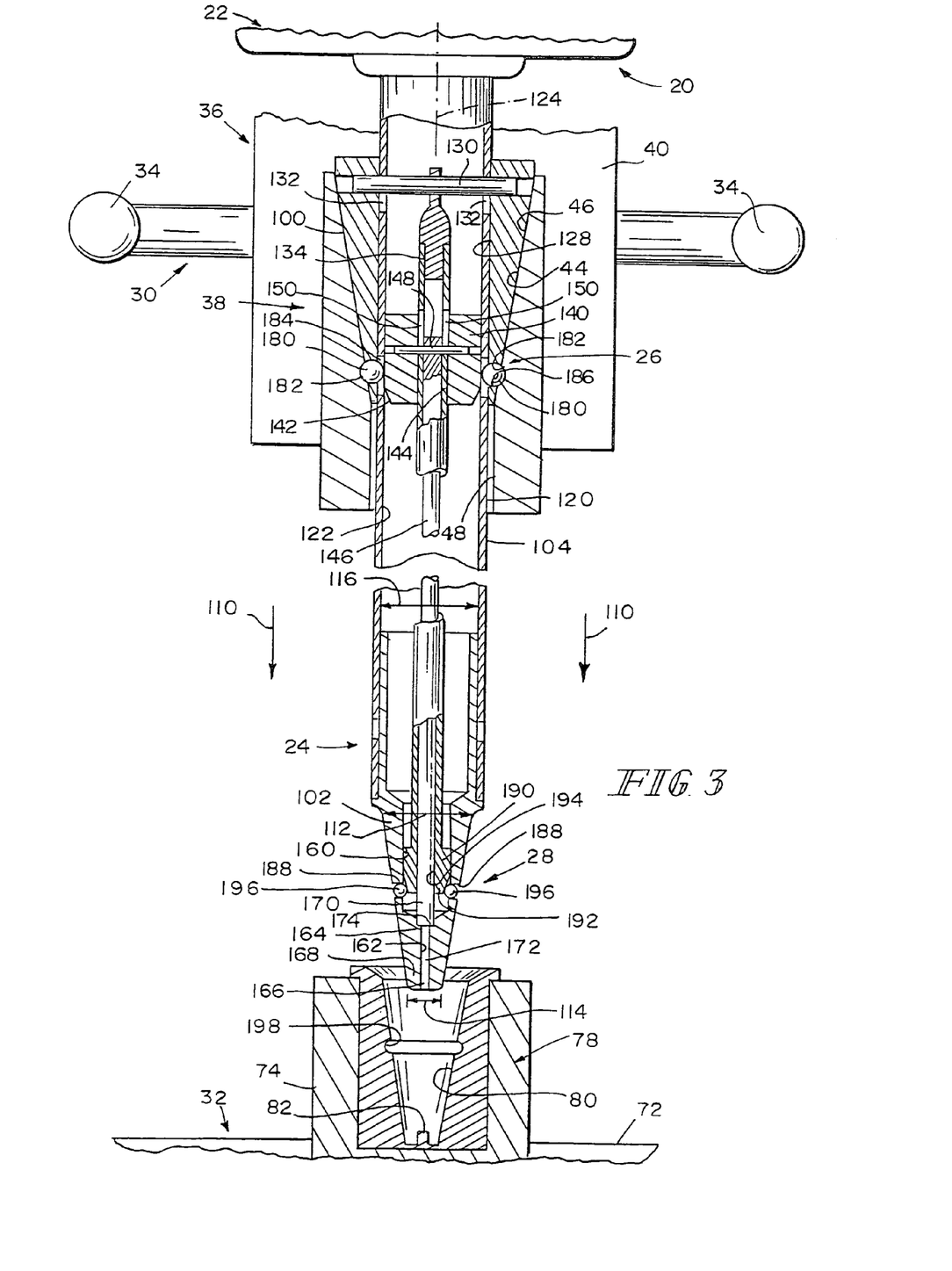
FIG. 3 is a sectional view of the post supported by column-mounted upper socket and locked thereto, and showing the post positioned over bed-mounted lower socket.

FIG. 1 shows an equipment support 20 having an equipment supporting portion 22 configured to support patient care equipment 23, a post 24 (also referred to herein as "coupler") coupled to equipment supporting portion 22 and extending downwardly therefrom and upper and lower locks 26, 28 (shown in FIG. 3). Patient care equipment 23 may be any one or more of the following: heart monitoring equipment, medical gas delivery equipment, infusion management equipment, equipment monitors, patient monitors, defibrillators, IV poles, and the like, many of which are directly connected to a patient via lines or tubes.

FIG. 2 shows equipment support 20 adapted to be transferable between a support structure, such as a column 30, and a patient support, such as a hospital bed 32. In FIG. 2, support structure is illustratively column 30 carried by a radial arm 31 mounted to a ceiling or a wall of a patient room of a hospital or a healthcare facility. However, it should be understood that support structure may very well be a stand, a cart, a headwall, a wall of a hospital room, and the like. Also, in FIG. 2, patient support is illustratively hospital bed 32 positioned in a patient room of a hospital or a healthcare facility. However, it should be understood that patient support may very well be a stretcher, a surgical table, an ambulatory care chair, and the like. Also, it should be understood that support structure and patient support may be used in different settings such as, for example, intensive care rooms, operating rooms and physician offices.

Column 30 includes a pair of handles 34, a bracket 36 and an upper tapered socket 38 (also referred to as "yoke"). Bracket 36 has a first telescoping portion 40 extending downwardly from column 30 and a second cantilevered portion 42 carrying upper socket 38. As shown in FIGS. 3 and 9, upper socket 38 has an upwardly opening bore 44. Bore 44 has an upper generally frustoconical portion 46 and a lower generally cylindrical portion 48. Upper frustoconical portion 46 varies in diameter from a large diameter to a small diameter in a downward direction. Upper socket 38 has a generally c-shaped cross section having spaced apart end portions 50, 52 which define an outwardly opening slot 54 in communication with bore 44. Spacing 56 between end portions 50, 52 of upper socket 38 is larger than the diameter 116 of a generally cylindrical intermediate portion 104 of post 24 to allow column-mounted upper socket 38 to pull away from post 24 after equipment support 20 is seated downwardly in a bed-mounted lower socket 78. Illustratively, U.S. Patent Application Publication No. US 2004/0199996 A1 discloses such equipment and is incorporated by reference herein.

Illustratively, first portion 40 of bracket 36 telescopes vertically relative to column 30 under the power of an electric motor (not shown) housed in column 30. Electric motor may be a Linak LA 31 Linear Actuator. Electric motor may be actuated by either a toggle switch (not shown) positioned on column 30, or a wired or wireless remote control. Such vertical telescoping movement of bracket 36 permits equipment support 20 to be raised and lowered for optimal positioning of patient care equipment 23 relative to a patient resting on a patient support. Also, such vertical telescoping movement of bracket 36 facilitates transfer of equipment support 20 between service column 30 and hospital bed 32. Additionally, such vertical telescoping movement permits the docking of equipment support 20 with a bed-mounted socket, as disclosed, for example, in U.S. Patent Application Publication No. US 2005/0000019-A1. which is incorporated by reference herein. Illustratively, bracket 36 may move as much as 12 to 18 inches (30.48 to 45.72 cm) relative to column 30.

Hospital bed 32 illustratively includes a lower frame 58 supported on casters 59, an upper frame 60 supported above lower frame 58 for movement relative to lower frame 58 between raised and lowered positions, a deck 62 supported above upper frame 60, and a mattress 64 supported by deck 62. An elevation adjustment mechanism 65 connects upper frame 60 to lower frame 58. Elevation adjustment mechanism 65 may be driven by a suitable actuator to cause upper frame 60 to move relative to lower frame 58. Although, upper frame 60 is movable relative to lower frame 58 in the illustrated embodiment, upper frame 60 need not be movable. Upper frame 60 includes a head-end frame member 66, which is configured to extend horizontally along the head end of upper frame 60. Illustratively, head-end frame member 66 extends beyond the outer periphery of deck 62, and supports push handles 68 and rolling bumpers 70.

A rail 72 is supported by frame member 66. A carriage 74 is coupled to rail 72 for movement along rail 72. Carriage 74 includes a lower tapered socket 78. Lower socket 78 has an upwardly opening frustoconical bore 80. As shown in FIG. 3, frustoconical bore 80 varies in diameter from a large diameter to a small diameter in a downward direction. Carriage 74 is lockable at any one of a plurality of locations 81 along rail 72. Lower socket 78 includes an upwardly extending upper lock release button 82. Illustratively, PCT Publication No. WO 2005/037164 discloses such a hospital bed and is incorporated by reference herein.

Post 24 includes a generally frustoconical upper tapered portion 100 (also sometimes referred to herein as "collar"), a generally frustoconical lower tapered portion 102 and a generally cylindrical intermediate portion 104 disposed between upper and lower tapered portions 100, 102. Upper tapered portion 100 varies in diameter from a large diameter 106 to a small diameter 108 in a downward direction 110. Lower tapered portion 102 varies in diameter from a large diameter 112 to a small diameter 114 in downward direction 110. Illustratively, small diameter 108 of upper tapered portion 100 is equal to or larger than large diameter 112 of lower tapered portion 102. Diameter 116 of cylindrical intermediate portion 104 may be equal to or smaller than small diameter 108 of upper tapered portion 100. In addition, diameter 116 of cylindrical intermediate portion 104 may be equal to or larger than large diameter 112 of lower tapered portion 102.

Figure 5:
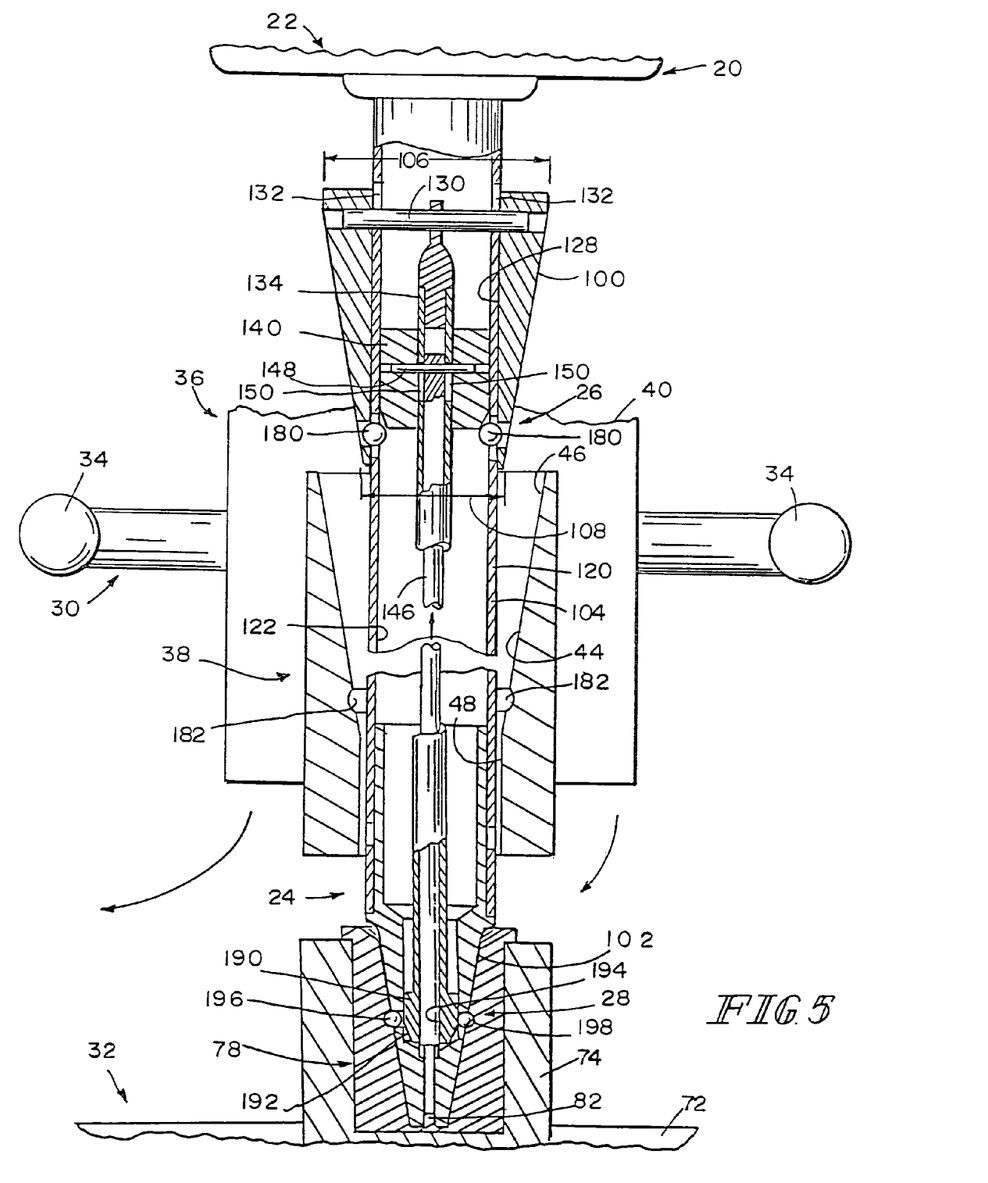
FIG. 5 is a sectional view of the post supported by the bed-mounted lower socket and locked thereto, and showing the upper socket lowered to a position below the upper portion of the post.

Upper and lower tapered portions 100, 102 of post 24 are configured for receipt in upper and lower tapered sockets 38, 78, respectively. The height of generally cylindrical intermediate portion 104 is greater than the height of upper socket 38. Also, diameter 116 of cylindrical intermediate portion 104 is smaller than spacing 56 between end portions 50, 52 of upper tapered socket 38. As shown in FIG. 5, these relationships allow service column 30 to pull away from post 24 after equipment support 20 is firmly seated in lower socket 78 and upper socket 38 is lowered to a position below upper tapered portion 100.

Figure 4:
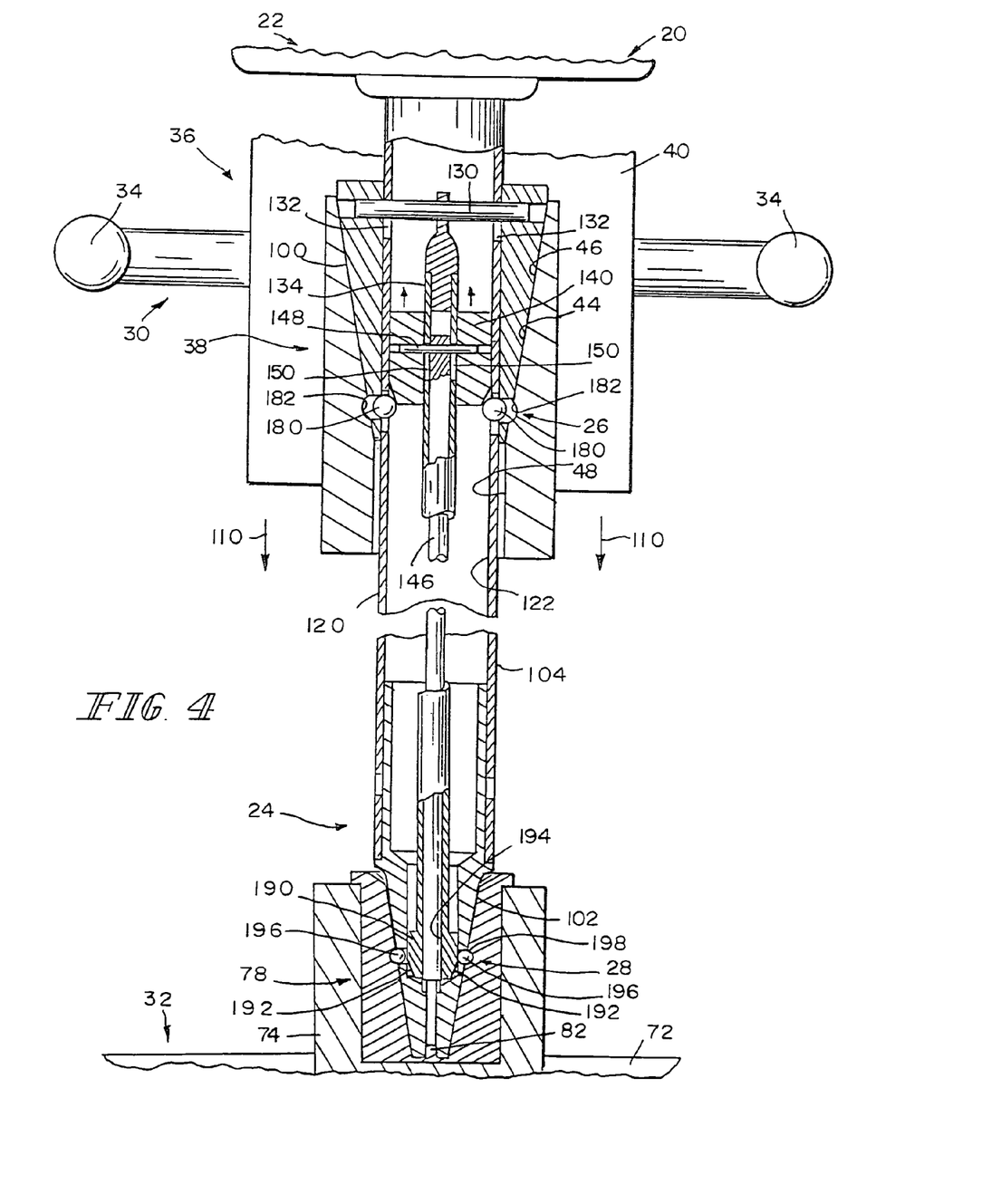
FIG. 4 is a sectional view of the post as it is transferred from the column-mounted upper socket to the bed-mounted lower socket and locked thereto.

Locks 26, 28 are configured to prevent accidental release of equipment support 20 from upper socket 38 until equipment support 20 is seated firmly in lower socket 78 and locked thereto. Likewise, locks 26, 28 are configured to prevent accidental release of equipment support 20 from lower socket 78 until equipment support 20 is seated firmly in upper socket 38 and locked thereto. As shown in FIG. 3, upper lock 26 is configured to move to a locking position to lock upper portion 100 to column-mounted upper socket 38 as lower lock 28 moves to an unlocking position to unlock lower portion 102 from bed-mounted lower socket 78. Likewise, as shown in FIG. 4, upper lock 26 is configured to move to an unlocking position to unlock upper portion 100 from column-mounted upper socket 38 as lower lock 28 moves to a locking position to lock lower portion 102 to bed-mounted lower socket 78.

Post 24 includes an outer tube 120 having a bore 122 defining a longitudinal axis 124. Upper portion 100 has a central bore 128. Upper portion 100 is sleeved over outer tube 120 for longitudinal movement relative thereto. A radially extending upper pin 130 is coupled to upper portion 100 and movably received in a pair of vertically extending upper slots 132 in outer tube 120. Upper slots 132 are longitudinally aligned and positioned on the opposite sides of outer tube 120. The height of slots 132 in post 24 define the extent of the vertical motion of upper portion 100 relative to post 24. An inner tube 134 is coupled to upper pin 130 and extends downwardly therefrom inside outer tube 120.

Upper lock 26 includes an upper locking cylinder 140 located within outer tube 120 for longitudinal movement therein. Upper locking cylinder 140 has a lower tapered portion 142 and a central bore 144. Tapered portion 142 varies in diameter from a large diameter to a small diameter in a downward direction. Upper locking cylinder 140 sleeves over inner tube 134 for longitudinal movement relative thereto. A rod 146 is coupled to upper locking cylinder 140 by means of a radially extending lower pin 148 and extends downwardly therefrom inside inner tube 134. Lower pin 148 extends through a pair of vertically extending lower slots 150 in inner tube 134. Lower slots 150 are longitudinally aligned and positioned on the opposite sides of inner tube 134.

Referring to FIG. 3, lower portion 102 of post 24 includes a first large diameter bore 160, a second small diameter bore 162, and an annular seat portion 164 formed at the juncture of large and small diameter bores 160, 162. Small diameter bore 162 terminates in an opening 166 near a bottom end 168 of lower portion 102. Rod 146 includes a first large diameter portion 170, a second small diameter portion 172, and an annular seat portion 174 formed at the juncture of large and small diameter portions 170, 172. Large diameter portion 170 of rod 146 is received in large diameter bore 160 in lower portion 102. Small diameter portion 172 of rod 146 is received in small diameter bore 162 in lower portion 102. Seat portion 174 of rod 146 normally rests against seat portion 164 of lower portion 102.

When rod 146 is resting against seat portion 164 of lower tapered portion 102, rod 146 supports upper locking cylinder 140 at an elevation where upper locking cylinder 140 drives upper locking balls 180 radially outwardly to engage an upper locking groove 182 in upper socket 38 to lock equipment support 20 to upper socket 38. When rod 146 is resting against seat portion 164, lower pin 148 is spaced away from a top end of vertically extending lower slots 150 in inner tube 134.

Outer tube 120 has a set of radially extending openings 184. Likewise, upper portion 100 has a set of radially extending openings 186 which are circumferentially aligned with corresponding openings 184 in outer tube 120. Upper locking balls 180 are received in radially extending openings 184, 186 for radial movement therein between the locking and unlocking positions. Upper locking balls 180 are retained in openings 186 in upper portion 100 by slightly deforming or peening the area around the openings 186. Illustratively, there are 4 locking balls 180 mounted in 4 equally spaced radial openings 184, 186.

Lower lock 28 includes a lower locking cylinder 190 coupled to inner tube 134 for longitudinal movement therewith. Lower locking cylinder 190 has a lower tapered portion 192 and a central bore 194. Tapered portion 192 varies in diameter from a large diameter to a small diameter in a downward direction. Lower locking cylinder 190 is received in large diameter bore 160 of lower portion 102. Lower locking cylinder 190 is sleeved over rod 146. When upper socket 38 supports upper portion 100 as shown in FIG. 3, upper pin 130 coupled to upper portion 100 supports inner tube 134 carrying lower locking cylinder 190 at an elevation where lower locking cylinder 190 allows lower locking balls 196 to move inwardly away from a lower locking groove 198 in lower socket 78 to prevent equipment support 20 from locking to lower socket 78. Also, when upper socket 38 supports upper portion 100, upper pin 130 is moved to a top end of vertically extending upper slots 132 in outer tube 120. Lower portion 102 has a set of radially extending openings 188. Lower locking balls 196 are received in radially extending openings 188 for radial movement therein between the locking and unlocking positions. Lower locking balls 196 are retained in openings 188 in lower portion 102 by slightly deforming or peening the area around the openings 188. Illustratively, there are 4 locking balls 196 mounted in 4 equally spaced radial openings 188.

As shown in FIG. 4, as equipment support 20 is seated downwardly in lower socket 78, upper lock release button 82 in lower socket 78 enters opening 166 in lower portion 102 near bottom end 168 thereof and lifts rod 146 upwardly. Rod 146, in turn, lifts lower pin 148, which, in turn, lifts upper locking cylinder 140 to an elevation where upper locking cylinder 140 allows upper locking balls 180 to move inwardly away from upper locking groove 182 in upper socket 38 to unlock equipment support 20 from upper socket 38.

Referring to FIGS. 3-5, as equipment support 20 is seated downwardly in lower socket 78, upper portion 100 moves downwardly with outer tube 120. As upper portion 100 moves downwardly, upper pin 130 coupled to upper portion 100 also moves downwardly. As upper pin 130 moves downwardly, inner tube 134 coupled to upper pin 130 and lower locking cylinder 190 coupled to inner tube 134 also move downwardly. Thus, as shown in FIGS. 4 and 5, as equipment support 20 is seated downwardly in lower socket 78, lower locking cylinder 190 moves downwardly to an elevation where lower locking cylinder 190 drives lower locking balls 196 radially outwardly to engage lower locking groove 198 in lower socket 78 to lock equipment support 20 to lower socket 78.

As equipment support 20 is seated downwardly in lower socket 78, rod 146 moves upwardly, and upper portion 100 and inner tube 134 move downwardly. As shown in FIG. 5, as upper portion 100 moves downwardly, upper pin 130 coupled to upper portion 100 also moves downwardly to a bottom end of vertically extending upper slots 132 in outer rube 120. As shown in FIGS. 4 and 5, as rod 146 moves upwardly and inner tube 134 moves downwardly, lower pin 148 coupled to rod 146 moves to top end of vertically extending lower slots 150 in inner tube 134.

Thus, as shown in FIGS. 3-5, to transfer equipment support 20 from column-mounted upper socket 38 to bed-mounted lower socket 78, the lower portion 102 of post 24 is generally aligned over lower socket 78 and column-mounted upper socket 38 is lowered to a position where upper socket 38 is below upper portion 100 of post 24. As equipment support 20 is seated downwardly in lower socket 78, upper lock release button 82 in lower socket 78 enters opening 166 in lower portion 102 and lifts rod 146 upwardly. Rod 146, in turn, lifts lower pin 148, which, in turn, lifts upper locking cylinder 140 to an elevation where upper locking cylinder 140 allows upper locking balls 180 to move inwardly away from upper locking groove 182 in upper socket 38 to unlock equipment support 20 from upper socket 38 as shown in FIGS. 4 and 5.

Also, as equipment support 20 is seated downwardly in lower socket 78, upper portion 100 moves downwardly with outer tube 120. As upper portion 100 moves downwardly, upper pin 130 coupled to upper portion 100 also moves downwardly. As upper pin 130 moves downwardly, inner tube 134 coupled to upper pin 130 and lower locking cylinder 190 coupled to inner tube 134 also move downwardly. Thus, as shown in FIGS. 4 and 5, as equipment support 20 is seated downwardly in lower socket 78, lower locking cylinder 190 moves downwardly to an elevation where lower locking cylinder 190 drives lower locking balls 196 radially outwardly to engage lower locking groove 198 in lower socket 78 to lock equipment support 20 to lower socket 78. When column-mounted upper socket 38 is lowered to a position where upper socket 38 is below upper portion 100 of post 24 as shown in FIG. 5, column 30 carrying upper socket 38 can be pulled away from post 24 by virtue of the fact that slot 54 in upper socket 38 is wider than diameter 116 of cylindrical intermediate portion 104 of post 24.

To transfer equipment support 20 from bed-mounted lower socket 78 to column-mounted upper socket 38, the sequence of steps is reversed. Referring to FIGS. 5, 4 and 3 in that order, upper socket 38 is positioned around intermediate portion 104 of post 24 and then raised to a position where upper socket 38 engages upper portion 100 of post 24 and lifts equipment support 20 off lower socket 78 permitting bed 32 to move away from column 30. Cylindrical intermediate portion 104 of post 24 is allowed to enter bore 44 in upper socket 38 through slot 54 therein. Again this is possible since slot 54 in upper socket 38 is wider than diameter 116 of cylindrical intermediate portion 104 of post 24.

As equipment support 20 is lifted off lower socket 78, rod 146 moves downwardly due to gravity until seat portion 174 of rod 146 rests against seat portion 164 of lower tapered portion 102. As shown in FIG. 3, as rod 146 moves downwardly, upper locking cylinder 140 coupled to rod 146 moves downwardly to an elevation where upper locking cylinder 140 drives upper locking balls 180 radially outwardly to engage upper locking groove 182 in upper socket 38 to lock equipment support 20 to upper socket 38.

As upper portion 100 is lifted by upper socket 38, upper pin 130 coupled to upper portion 100 and inner tube 134 coupled to upper pin 130 move upwardly. As shown in FIG. 3, as inner tube 134 moves upwardly, lower locking cylinder 190 coupled to inner tube 134 moves upwardly to an elevation where lower locking cylinder 190 allows lower locking balls 196 to move inwardly away from a lower locking groove 198 in lower socket 78 to unlock equipment support 20 from lower socket 78. When upper socket 38 supports upper portion 100, upper pin 130 is moved to a top end of vertically extending upper slots 132 in outer tube 120. As equipment support 20 is lifted off lower socket 78, bed 32 can be pulled away from column 30.

Figure 6:
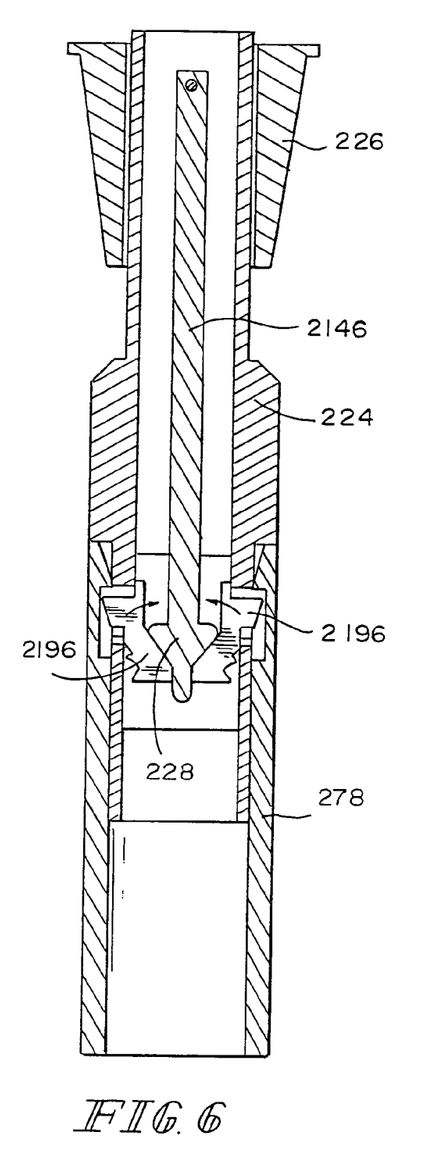
FIGS. 6-8 are sectional views showing alternative embodiments of lock mechanisms incorporated in the FIG. 1 equipment support.
Figure 7:
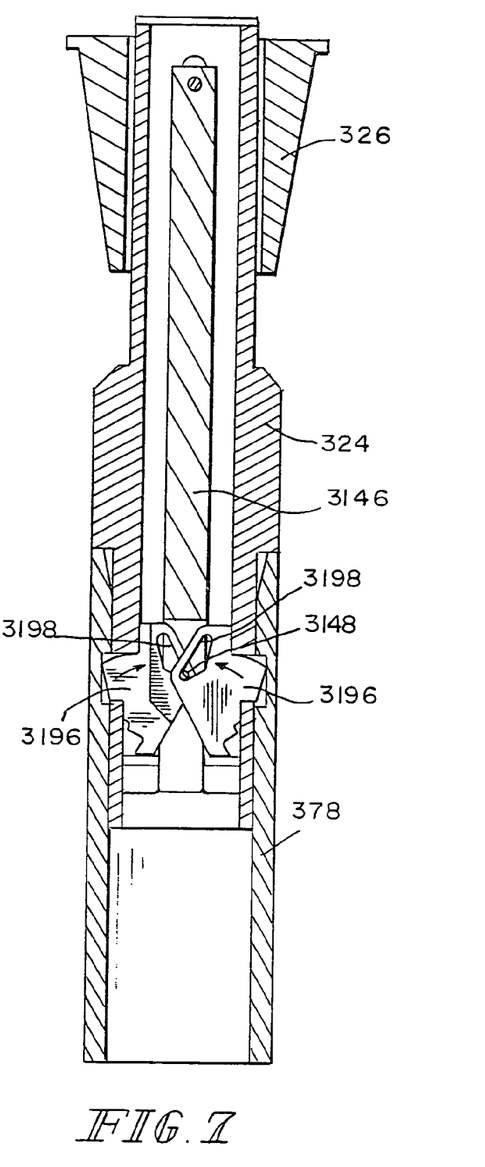
Figure 8:
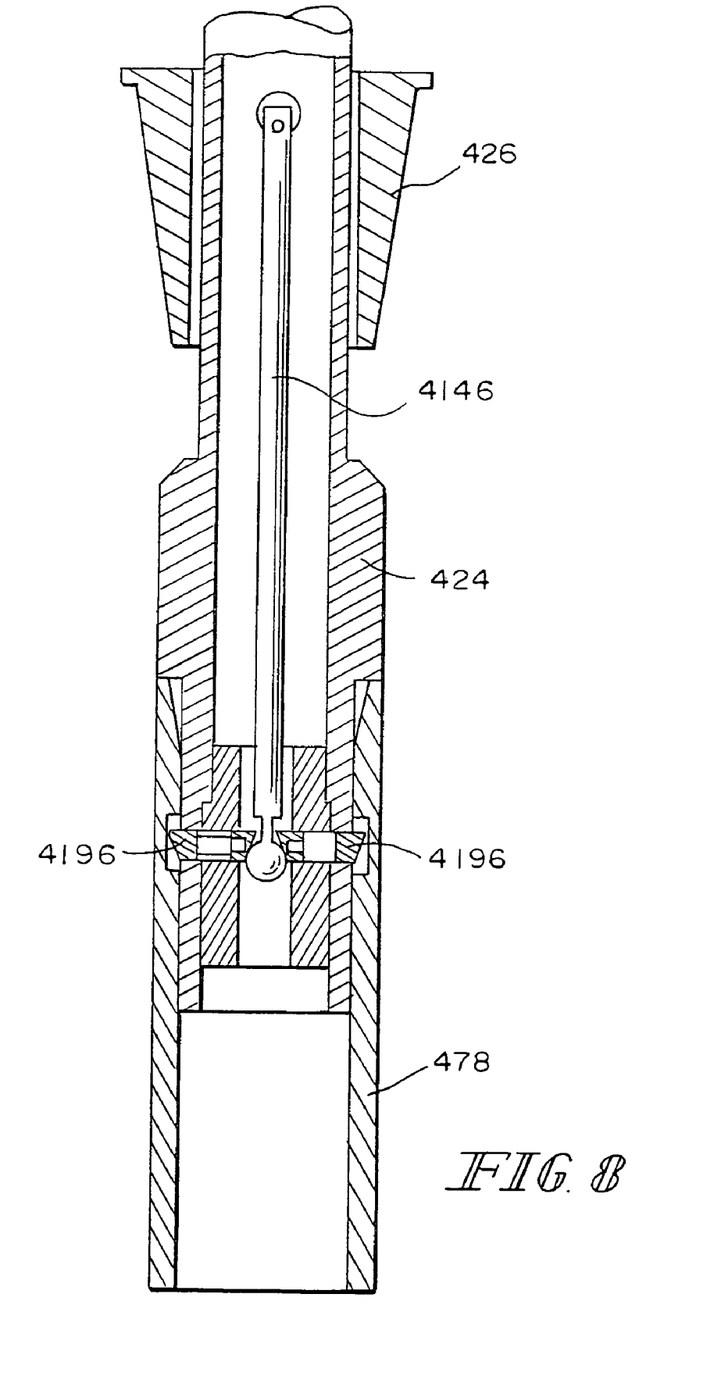

FIGS. 6-8 show alternate latch mechanisms that can be used in lieu of latch mechanisms employing locking cylinders 140, 190, locking balls 180, 196 and locking grooves 182, 198 shown in FIGS. 3-5. Referring to FIG. 6, as a post 224 is seated downwardly in a bed-mounted lower socket 278, cams 2196 are spring loaded to automatically lock post 224 to lower socket 278. To disengage post 224 from lower socket 278, the user pushes down on a collar 226 that is coaxially mounted on post 224. A rod 2146 located inside post 224 connects collar 226 to a conical plunger 228. As collar 226 is pushed down, conical plunger 228 engages spring-loaded cams 2196 to rotate them out of the way. Post 224 is now free to be lifted out of lower socket 278.

Referring to FIG. 7, as post 324 is seated downwardly in bed-mounted lower socket 378, cams 3196 are spring loaded to automatically lock post 324 to lower socket 378. To disengage post 324 from lower socket 378, the user pulls up on a tapered collar 326 which, in turn, pulls up on a rod 3146. A cross pin 3148 coupled to rod 3146 rides in respective slots 3198 in cams 3196. As collar 326 is pulled up, cross pin 3148 rotates spring-loaded cams 3196 out of the way. Post 324 is now free to be lifted out of lower socket 378. Collar 326 can be configured to cooperate with a lifting device so that post 324 is automatically freed from lower socket 378 as equipment support 20 is lifted off lower socket 378.

Referring to FIG. 8, as post 424 is seated downwardly in bed-mounted lower socket 478, cam elements 4196 are spring loaded to automatically lock post 424 to lower socket 478. To disengage post 424 from lower socket 478, the user pulls up on a tapered collar 426 which, in turn, pulls up on a rod 4146. As collar 426 is pulled up, cam elements 4196 are retracted out of the way. Post 424 is now free to be lifted out of lower socket 478. Collar 426 can be configured to cooperate with a lifting device so that post 424 is automatically freed from lower socket 478 as equipment support 20 is lifted off lower socket 478.

Although the invention has been described in detail with reference to certain illustrative embodiments, variations and modifications exist with the scope and spirit of this disclosure as described and defined in the following claims.

The invention claimed is:

1. An equipment support transferable between a first device having an upper socket and a second device having a lower socket, the equipment support comprising:
   an equipment supporting portion configured to support patient care equipment,
   a downwardly extending coupler coupled to the equipment supporting portion, the coupler having upper and lower portions configured for receipt in the upper and lower sockets, respectively, and
   upper and lower locks, the upper lock moving to a locking position to lock the upper portion to the upper socket as the lower lock moves to an unlocking position to unlock the lower portion from the lower socket, and the upper lock moving to an unlocking position to unlock the upper portion from the upper socket as the lower lock moves to a locking position to lock the lower portion to the lower socket.

2. The equipment support of claim 1, wherein each of the upper and lower locks comprises a locking element and a locking member that moves to wedge the locking element against the respective one of upper and lower sockets when the upper and lower locks are in their respective locking positions.

3. The equipment support of claim 2, wherein the lower portion of the coupler has an opening at a bottom end thereof, the upper lock comprises a rod coupled to the upper locking member and extending downwardly therefrom, and an end of the rod spaced from the upper locking member is accessible through the opening.

4. The equipment support of claim 3, wherein the lower socket comprises a protrusion that engages the rod and enters the opening as the lower portion seats downwardly into the lower socket.

5. The equipment support of claim 3, wherein the coupler comprises a tube having a bore, and the upper locking member and the rod are received in the bore of the tube.

6. The equipment support of claim 1, wherein each of the coupler upper and lower portions varies in diameter from a large diameter to a small diameter in a downward direction, and the small diameter of the upper portion is equal to or larger than the large diameter of the lower portion.

7. The equipment support of claim 6, wherein each of the coupler upper and lower portions is frustoconical.

8. The equipment support of claim 1, wherein the coupler has a generally cylindrical intermediate portion between the upper and lower portions.

9. The apparatus of claim 8, wherein the upper socket has a generally c-shaped cross section having spaced apart end portions which define an outwardly opening slot in communication with a bore in the upper socket, and the spacing between the end portions of the upper socket is larger than the diameter of the generally cylindrical intermediate portion of the coupler.

10. The apparatus of claim 9, wherein the height of the generally cylindrical intermediate portion is greater than the height of the upper socket.

11. The apparatus of claim 10, wherein the equipment support is transferred from the first device to the second device as the upper socket carrying the equipment support is lowered while the lower portion of the coupler is generally aligned with the lower socket to a position where the upper socket is below the upper portion of the coupler permitting the lower socket to carry the equipment support and allowing the first device to move away from the second device.

12. The apparatus of claim 11, wherein the equipment support is transferred from the second device to the first device as the upper socket is positioned around the intermediate portion of the coupler and then raised to a position where the upper socket engages the upper portion of the coupler and lifts the equipment support off the lower socket permitting the second device to move away from the first device.

13. The equipment support of claim 1, wherein the first device comprises any one of the following: an arm, a column, a cart, a stand, a hospital bed, a surgery table and a stretcher.

14. The equipment support of claim 1, wherein the second device comprises any one of the following: an arm, a column, a cart, a stand, a hospital bed, a surgery table and a stretcher.

15. The equipment support of claim 1, wherein the equipment support comprises one of an IV pole and a rack adapted to carry infusion equipment.

16. The equipment support of claim 1, wherein the upper lock includes an upper locking element movable between the locking position where the upper locking element engages the upper socket to block the upper portion from moving relative to the upper socket and the unlocking position where the upper locking element disengages from the upper socket to free the upper portion to move relative to the upper socket.

17. The equipment support of claim 16, wherein the coupler comprises an outer tube having a longitudinal axis and a radially extending opening, the upper portion comprises a collar placed about the outer tube for movement along the longitudinal axis, the collar has a radially extending opening generally aligned with the radially extending opening in the outer tube, and the upper locking element is positioned in the radially extending openings in the outer tube and the collar for radial movement therein between the locking and unlocking positions.

18. The equipment support of claim 17, wherein the upper portion comprises a radially extending pin coupled to the collar and movably received in a generally vertically extending slot in the outer tube, the upper socket supports the equipment support when the radially extending pin moves to a top end of the vertically extending slot in the outer tube, and the lower socket supports the equipment support when the radially extending pin moves to a bottom end of the vertically extending slot in the outer tube.

19. The equipment support of claim 16, wherein the lower lock includes a lower locking element movable between its locking position where the lower locking element engages the lower socket to block the lower portion from moving relative to the lower socket and its unlocking position where the lower locking element disengages from the lower socket to free the lower portion to move relative to the lower socket.

20. The equipment support of claim 19, wherein the lower portion includes a radially extending opening in communication therewith, and the lower locking element is positioned in the radially extending opening for radial movement therein between the locking and unlocking positions thereof.

21. The equipment support of claim 19, wherein the lower lock includes a lower locking cylinder located within an interior region of the lower portion for longitudinal movement therein, the lower locking cylinder has a first outer diameter and a second outer diameter small than the first outer diameter, the portion of the lower locking cylinder having the first outer diameter engages the lower locking element to move the lower locking element outwardly to its locking position, and the portion of the lower locking cylinder having the second outer diameter allows the lower locking element to move inwardly to its unlocking position.

22. The equipment support of claim 21, wherein the coupler comprises an outer tube having a longitudinal axis and a generally vertically extending slot, the upper portion comprises a collar placed about the outer tube and a radially extending pin coupled to the collar and movably received in the generally vertically extending slot in the outer tube, the lower lock comprises an inner tube coupled to the radially extending pin and extending downwardly therefrom, and the lower locking cylinder is coupled to the inner tube for movement therewith.

23. The equipment support of claim 22, wherein the upper lock includes an upper locking cylinder located within the outer tube for longitudinal movement therein, the lower portion of the coupler has an opening at a bottom end thereof, the upper lock comprises a rod positioned inside the inner tube, the rod is coupled to the upper locking cylinder and extends downwardly therefrom, an end of the rod spaced from the upper locking member is accessible through the opening, and the rod engages a stop as the lower portion of the coupler seats downwardly in the lower socket to unlock the upper portion from the upper socket.

24. The equipment support of claim 16, wherein the coupler comprises an outer tube having a longitudinal axis and a bore, the upper lock includes an upper locking cylinder located within the bore for longitudinal movement therein, the upper locking cylinder has a first outer diameter and a second outer diameter smaller than the first outer diameter, the portion of the upper locking cylinder having the first outer diameter engages the upper locking element to move the upper locking element outwardly to its locking position, and the portion of the upper locking cylinder having the second outer diameter allows the upper locking element to move inwardly to its unlocking position.

25. The equipment support of claim 24, wherein the lower portion of the coupler has an opening at a bottom end thereof, the upper lock comprises a rod coupled to the upper locking cylinder and extending downwardly therefrom, an end of the rod spaced from the upper locking member is accessible through the opening, and the rod engages a portion of the lower socket and enters the opening as the lower portion of the coupler seats downwardly in the lower socket to unlock the upper portion from the upper socket.

26. A patient care equipment support transferable between a first device having an upper tapered socket and a second device having a lower tapered socket, the equipment support comprising:

an equipment supporting portion configured to support patient care equipment,     a downwardly extending coupler coupled to the equipment supporting portion, the coupler having upper and lower tapered portions configured for receipt in the upper and lower tapered sockets, respectively, and     upper and lower locks, the upper lock moving to a locking position to lock the upper tapered portion to the upper tapered socket as the lower lock moves to an unlocking position to unlock the lower tapered portion from the lower tapered socket, and the upper lock moving to an unlocking position to unlock the upper tapered portion from the upper tapered socket as the lower lock moves to a locking position to lock the lower tapered portion to the lower tapered socket.

* * * * *